United States Patent [19]

Kikuchi et al.

[11] Patent Number: 4,841,990
[45] Date of Patent: Jun. 27, 1989

[54] APPLICATOR FOR USE IN HYPERTHERMIA

[75] Inventors: Makoto Kikuchi, Mitaka; Shinsaku Mori, Tokyo; Yoshio Nikawa, Tokyo; Takashige Terakawa, Tokyo, all of Japan

[73] Assignee: Tokyo Keiki Co., Ltd., Tokyo, Japan

[21] Appl. No.: 878,329

[22] Filed: Jun. 25, 1986

[30] Foreign Application Priority Data

Jun. 29, 1985 [JP] Japan ................... 60-143549
Jun. 29, 1985 [JP] Japan ................... 60-143550
Jun. 29, 1985 [JP] Japan ................... 60-143551

[51] Int. Cl.$^4$ ........................................... A61N 5/00
[52] U.S. Cl. ..................... 128/804; 219/10.55 F; 219/.10.55 R
[58] Field of Search ............... 128/804, 399; 219/10.55 A, 10.55 F, 10.55 R

[56] References Cited

U.S. PATENT DOCUMENTS

| | | | |
|---|---|---|---|
| 3,077,195 | 2/1963 | Folsche | 128/804 |
| 3,288,894 | 11/1966 | Deaton | 219/10.55 F |
| 4,140,130 | 2/1979 | Storm | 128/804 |
| 4,228,809 | 10/1980 | Paglione | 128/804 |
| 4,282,887 | 8/1981 | Sterzer | 128/804 |
| 4,397,313 | 8/1983 | Vaguine | 128/399 |
| 4,397,314 | 8/1983 | Vaguine | 128/399 |
| 4,462,412 | 7/1984 | Turner | 128/804 |
| 4,586,516 | 5/1986 | Tuner | 128/804 |
| 4,589,424 | 5/1986 | Vaguine | 128/399 |

FOREIGN PATENT DOCUMENTS

| | | | |
|---|---|---|---|
| 1111386 | 6/1984 | European Pat. Off. | |
| 1440333 | 4/1969 | Fed. Rep. of Germany | |
| 2417263 | 10/1975 | Fed. Rep. of Germany | 128/804 |

OTHER PUBLICATIONS

Vetter, "Linear Tuning . . . Cavity" IEEE Trans. on Microwave Theory & Techniques, Nov. 1965, p. 880.
Magin, "IEEE Trans. Microwave Theory & Tech.", MTT 27, No. 1, pp. 78-83, Jan. 1979.
Robinson et al., "IEEE Trans. Microwave Theory & Tech.", MTT-26, No. 8, pp. 546-549, Aug. 1978.
*Hyperthermia in Cancer Therapy*, Storm, G. K. Hull, Med. Pub., 1983.
Astrahan et al., IEEE Trans. Microwave Theory & Tech., MTT 26, No. 18, pp. 546-549, Aug. 1978.

*Primary Examiner*—Lee S. Cohen
*Attorney, Agent, or Firm*—Sandler & Greenblum

[57] ABSTRACT

The applicator of this invention functions as an antenna of electromagnetic waves when used in hyperthermia. The casing of this applicator serves as waveguide.

The applicator incorporates in its casing an electromagnetic lens. It is also provided with a cooling mechanism for cooling the body surface of the heated region at an opening of the casing. When electromagnetic waves which have been introduced from outside to the supply portion propagate in the human body from the opening of the casing, energy reflection is generated due to untuned impedance. In order to prevent this reflection, the applicator of this invention incorporates three stub tuners which can be adjusted from outside so as to reduce the loss of energy.

The casing of the applicator of this invention is filled with fluid such as machine oil which has a small damping factor so as to reduce the loss of electromagnetic waves in the casing which occurs during its propagation. The three stub tuners are waterproofed at their movable portion. Change in temperature is dealt with by providing a fluid accommodating means.

6 Claims, 9 Drawing Sheets

APPLICATOR FOR USE IN HYPERTHERMIA

BACKGROUND OF THE INVENTION

1. Field of the Invention

The present invention relates to an applicator for use in hyperthermia, and, more particularly, to an applicator for use in hyperthermia which is used to treat a predetermined location within a human body by locally applying heat thereto by means of electromagnetic waves.

2. Prior Art

Lately, hyperthermia has been attracting attention. Recent researches (including that reported on Page 14 of MICROWAVES, October, 1976) have shown that, if heat is continuously applied to a malignant tumor at a temperature of about 43° C. for an hour or two, and this application of heat is repeated at regular intervals, it is possible to impede the regeneration of cancer cells and simultaneously kill most of them. Hyperthermia of this type falls into two categories: general hyperthermia and local hyperthermia. In local hyperthermia, in which cancerous tissue and its surroundings are selectively heated, methods using electromagnetic waves, electromagnetic induction, or ultrasonic waves have been proposed.

Figure 1:
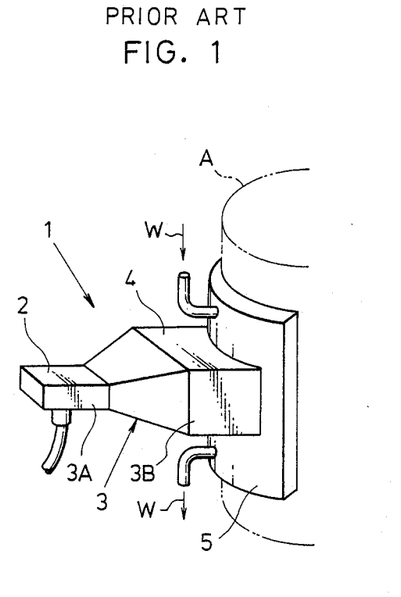
FIG. 1 is a perspective view of a conventional applicator.

The present inventors have proposed and are containing to research the treatment of cancers located deep in the human body by means of electromagnetic waves. In such treatment, it is necessary to focus the electromagnetic energy when transmitting the electromagnetic waaves into the body. For this purpose, the present inventors have incorporated an electromagnetic lens in a heating applicator. An applicator 1 adopted by the present inventors, as shown in FIG. 1, is composed of a casing 3 which functions as a waveguide, a wave supply portion 2 provided at one end of the casing 3, and an electromagnetic lens portion 4 provided at the other end of the casing 3. The output side of the electromagnetic lens portion 4 is provided with a solid cooling plate 5 which prevents the surface of the body from overheating, and which employs cooling water.

However, this conventional applicator suffers from the following disadvantages:

(1) In the applicator, electromagnetic waves are reflected by the electromagnetic lens or coolant, generating a large amount of energy loss of electromagnetic waves. This causes the output of the applicator to be lowered.

(2) Loss of electromagnetic wave energy occurring in the applicator causes the applicator to overheat, making the handling of the applicator difficult.

(3) The raised temperature of the applicator invites thermal expansion of the fluid such as machine oil which is accommodated in the applicator. This can lead to damage of the applicator.

SUMMARY OF THE INVENTION

Accordingly, an object of the present invention is to provide an applicator for use in hyperthermia which is capable of irradiating electromagnetic wave energy continuously and efficiently by employing an electromagnetic lens to locally treat cancerous tissue formed in the human body.

A further object of the present invention is to provide an applicator for use in hyperthermia which is capable of effectively preventing the impedance in the applicator from becoming out of tune and thereby reducing the energy loss of electromagnetic waves which is caused by the reflected electromagnetic waves inside the applicator.

A still further object of the present invention is to provide an applicator for use in hyperthermia which is improved in durability in the face of the changes in temperature.

DETAILED DESCRIPTION

First Embodiment

A first embodiment of the present invention will now be described with reference to FIGS. 2 to 12.

Figure 2:
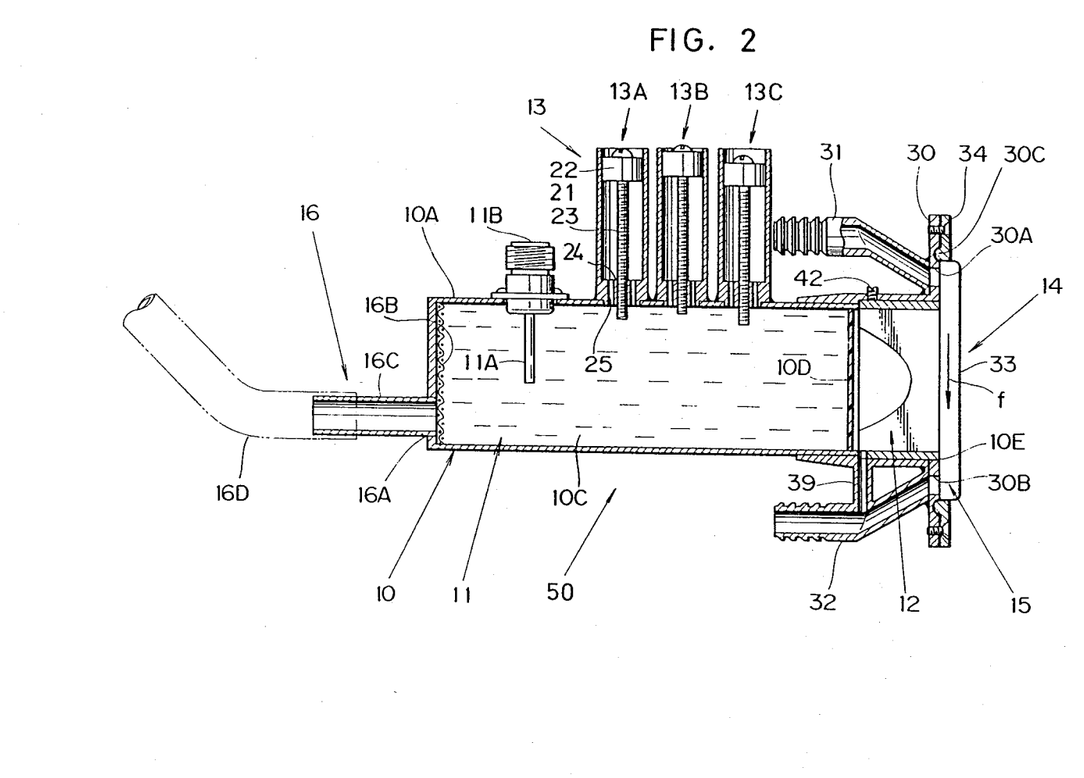
FIG. 2 is a sectional view of a first embodiment of the present invention, showing the applicator including coolant guides.
Figure 3:
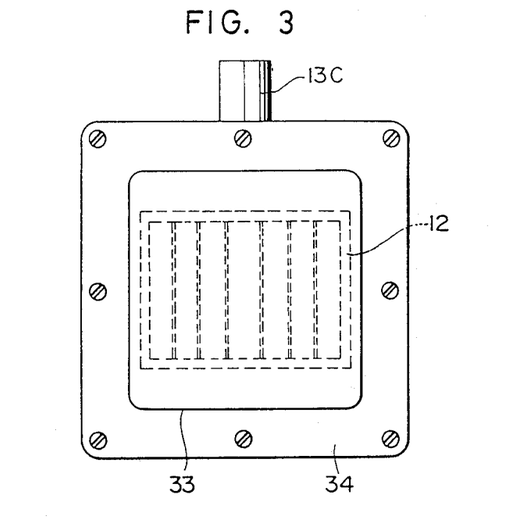
FIG. 3 is a side elevational view of the applicator shown in FIG. 2, as viewed from the right in FIG. 2.
Figure 4:
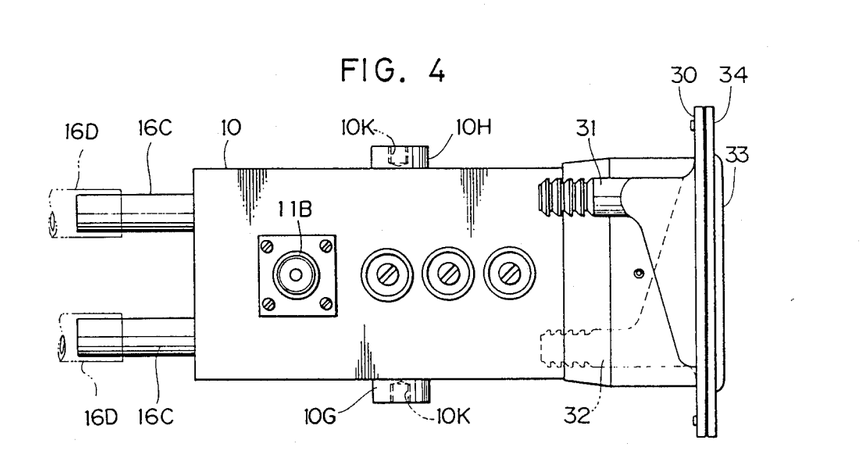
FIG. 4 is a plan view of the applicator shown in FIG. 2.
Figure 5:
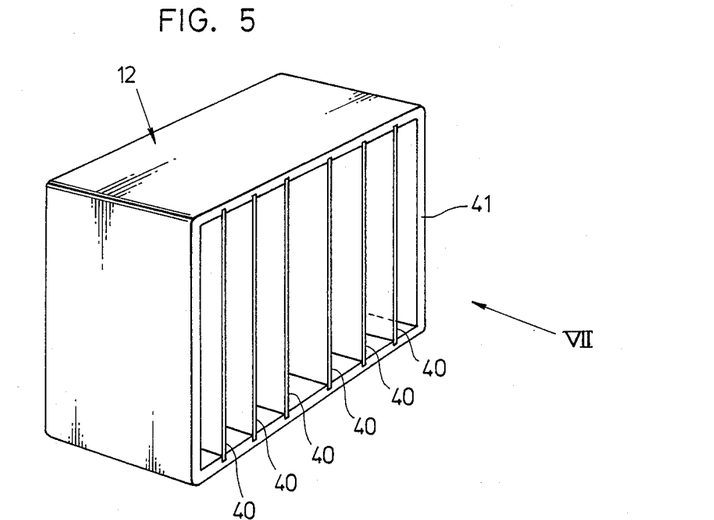
FIGS. 5 and 6 are perspective views of the electromagnetic lens portion employed in the applicator shown in FIG. 2.
Figure 6:
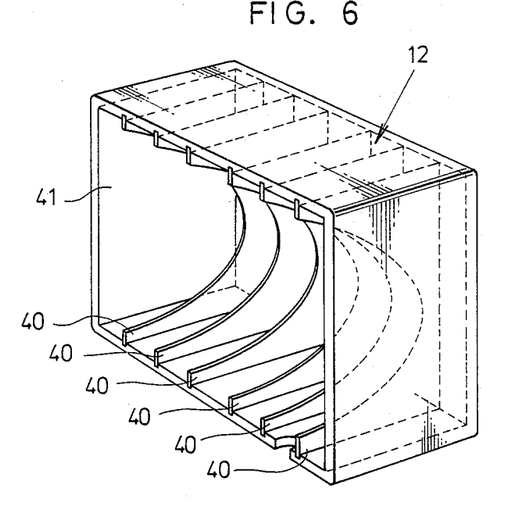

Referring first to FIG. 2, reference numeral 10 denotes a casing which functions as a waveguide. The casing 10, as shown in FIGS. 2 and 3, is in the shape of a box, and is provided with an electromagnetic wave supply portion 11 at one end thereof, an electromagnetic lens portions 12 at the other end thereof, and a stub tuner mechanism 13 for tuning electromagnetic waves at an intermediate portion thereof. The right end of the electromagnetic lens portion 12, as viewed in FIG. 2, forms an open electromagnetic wave-radiating end portion 14. A cooling mechanism 15 for cooling the surface of the human body is provided in the electromagnetic wave-radiating end portion 14 in such a manner that it covers the end portion 14 from the outside.

The electromagnetic wave supply portion 11 includes a supply portion waveguide 10A which is a component of the casing 10, a driving antenna 11A protruding from the central portion of the supply portion waveguide 10A, and a waterproof coaxial connector 11B for electromagnetic waves which is connected to the driving antenna 11A. This construction ensures that electromagnetic waves transmitted through the coaxial connector 11B are efficiently introduced into the casing 10.

The supply portion waveguide 10A is filled with insulating oil (hereinafter referred to merely as "oil") 10C which has a small damping factor with respect to electromagnetic waves, including the portion where the sub tuner mechanism 13 is mounted. An oil sealing screen 10D made of a dielectric material is provided so as to seal in the oil 10C.

The stub tuner mechanism 13 of this embodiment employs three stub tuners disposed at predetermined intervals in alignment with each other. To be specific, stub tuners 13A, 13B and 13C each include a cylinder portion 21 with one open end, a liquid proof piston member 22 which moves back and forth in the cylinder portion 21, a screw member 23 which is integrally formed with the piston member 22 and which has a a stub-tuning function, a screw hole 24 through which the screw member 23 is threaded, and at least one through-hole 25 communicating the interiors of the casing 10 and the cylinder portion 21. Each screw member 23 is rotated so that it protrudes a suitable amount into the casing 10, thereby providing the required tuning.

In this case, the through-hole 25 constitutes a hole through which the oil 10C circulates as a result of the reciprocal motion of the piston member 22.

An oil release mechanism 16 is provided in a part of the supply portion waveguide 10A so as to enable the smooth circulation of the oil 10C, i.e., the smooth reciprocal motion of the piston members 22, as well as to enable thermal expansion of the oil due to overheating of the casing as a result of the continuous use thereof.

The oil release mechanism 16 of this embodiment includes through-holes 16A, 16A provided at two positions of the supply portion waveguide 10A at a predetermined spacing, wire mesh 16B which has a relatively small mesh size and which is disposed inside the supply portion waveguide 10A in such a manner that it covers the through-holes 16A from the inside, guide tubes 16C, 16C connected to the respective through-holes 16A, 16A, and oil release tubes 16D, 16D made of a relatively soft material which are connected to the respective guide tubes 16C, 16C and extend upward. The guide tubes 16C and oil release tubes 16D together constitute a fluid guide means. The wire mesh 16B forms part of the side wall of the electromagnetic wave supply portion 11. Therefore, it may be replaced with, for example, a plurality of small holes provided directly in the inner wall of the electromagnetic wave supply portion 11, if they can be made to function in the same manner. A plate-like metal member having a large number of small through-holes may also be employed in place of the wire mesh 16B.

The cooling mechanism 15 provided at the electromagnetic wave-radiating end portion 14 of the casing 10 is made flat in order to be able to cool the surface of the heated portion efficiently. To be more specific, the cooling mechanism 15 includes a base plate 30 which is integrally secured to the casing 10, a rectangular coolant inlet 30A provided on one edge of the base plate 30, a corresponding rectangular coolant outlet 30B provided on the other edge of the base plate 30, an insulating film waterproofing groove 30C which is provided in such a manner that it surrounds the coolant inlet and outlet 30A and 30B as well as an aperture 10E in the electromagnetic wave-radiating end portion 14, coolant guides 31 and 32 connected to the coolant inlet 30A and outlet 30B, respectively, a flat insulating film member 33 disposed in such a manner that it covers substantially the entire surface of the electromagnetic wave-radiating end portion 14, and a frame plate 34 for mounting the insulating film member 33 onto the base plate 30 in a state wherein the periphery of the insulating film member 33 is waterproofed and the insulating film member can be easily removed. The insulating film member 33 is in the form of a dish with its outer side raised and its inner side open, and is made of a film-shaped dielectric which has a small damping factor with respect to electromagnetic waves. The cooling water which flows in through the inlet 30A moves over the inside of the insulating film member 33 and out through the outlet 30B, as shown by the arrow f in FIG. 2. During this time, it cools the surface of the body efficiently through the intermediary of the insulating film member 33.

The electromagnetic lens portion 12, provided at the right end of the casing 10 as viewed in FIG. 2, is formed into a box with two opposite sides open, as shown in FIGS. 5 to 9. It is detachably housed in the casing 10.

Figure 7:
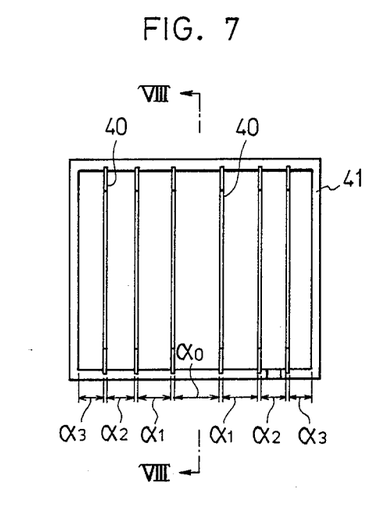
FIG. 7 is a front view of the electromagnetic lens portion, when looking in the direction of the arrow VII in FIG. 5.
Figure 8:
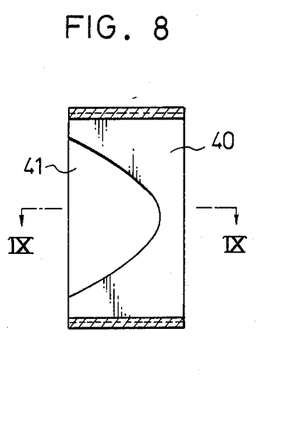
FIG. 8 is a section taken along the line VIII—VIII of FIG. 7.
Figure 9:
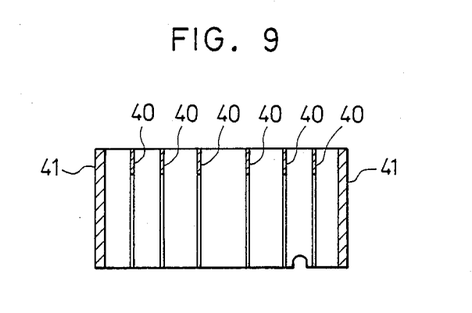
FIG. 9 is a section taken along the line IX—IX of FIG. 8.
Figure 10:
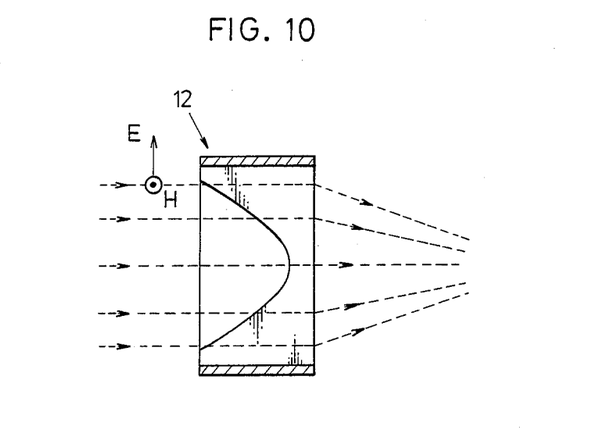
FIGS. 10 and 11 each illustrate how the electromagnetic waves are focused.
Figure 11:
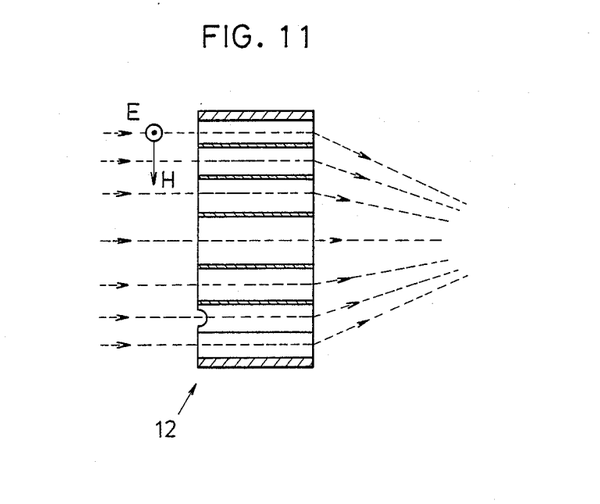
Figure 12:
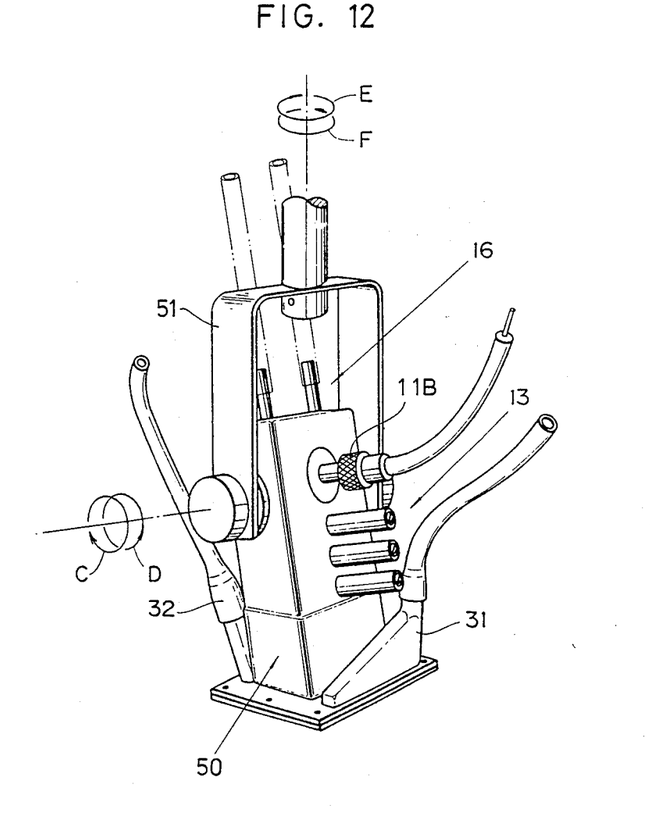
FIG. 12 is a perspective view of the applicator shown in FIG. 2, showing how it is mounted when used.

To be more specific, the electromagnetic lens portion 12 includes a plurality of metal plates 40, 40 of the same dimensions and a frame 41 for locking the upper and lower edges of the metal plates 40, as viewed in FIG. 7. The metal plates 40 are spaced apart from each other at intervals, as shown in FIG. 7, which are at maximum of $\alpha_0$ at the center and which become gradually smaller with a dimension of $\alpha_1$, $\alpha_2$, and $\alpha_3$ (where $\alpha_0 > \alpha_1 > \alpha_2 > \alpha_3$) closer to the side walls of the frame 41. This overall arrangement of the metal plates provides the received electromagnetic waves with a predetermined lens effect in one direction, as shown by the dotted lines in FIG. 11. The central portion of the edge of each metal plate 40 which faces the electromagnetic wave supply portion 11 is cut out in an arcuate shape, so as to provide the same electromagnetic waves with a predetermined lens effect in another direction which is perpendicular to the first direction, as shown in FIG. 10. FIG. 12 shows the thus-arranged electromagnetic lens portion 12 accommodated in the casing 10, as seen when looking from the right side of FIG. 2 (with the insulating film member 33 removed therefrom). In this case, the electromagnetic lens portion 12 is open on both its electromagnetic wave reception and radiating sides so as to enable the coolant in the cooling mechanism 15 to easily flow into and out of the electromagnetic lens portion.

The electromagnetic lens portion 12 is locked by means of a setscrew 42, as shown in FIG. 2. The box-shaped electromagnetic lens portion 12 is detachably mounted, as previously described. As affected part may be located at any depth in the body, so several tens of lens portions 12 are prepared beforehand, and a suitable lens portion is selected to suit the depth of the affected part to be treated.

The electromagnetic lens portion 12 is provided with a pipe 39 of a relatively small diameter, on the side thereof which faces the electromagnetic wave supply portion 11. The pipe 39 communicates with the coolant guide 32 through which the coolant flows out, and acts as a bubble-releasing means through which bubbles generated during the treatment are directly sucked away through the coolant guide 32 by the vacuum pressure generated as the result of the flow of coolant.

The thus-constructed applicator 50 of this embodiment for use in hyperthermia is retained by support members 10G and 10H provided at both sides thereof, in an applicator retaining means 51 which has an inverted U-shaped configuration, in such a manner that it can be pivoted freely, as shown by the arrows C and D in FIG. 12. The applicator retaining means 51 is supported by a support mechanism (not shown) so that it can be rotated as shown by the arrows E and F, thereby ensuring that the applicator can assume any position to suit the affected part being treated.

Operation of the first embodiment will now be described below.

The electromagnetic waves which are input through the coaxial connector 11B and output toward the inside of the casing 10 by the driving antenna 11A are transmitted to the electromagnetic lens portion 12 without being damped while propagating in the oil 10C. As they propagate through the electromagnetic lens portion 12, the waves passing through the outer portion moves faster than those passing through the central portion so that they are focused at the same time that they are radiated from the electromagnetic lens portion 12. The electromagnetic waves which have been focused by the lens portion, after they pass through the cooling mechanism 15, propagate from the surface of the body toward the human body, with some of them being reflected by the surface of the body and the remaining ones acting to heat the body surface and deeper regions thereof. At this time, the surface of the body is efficiently cooled by the cooling mechanism 15. The point of focus at a predetermined depth and its surroundings can be effectively heated, since the electromagnetc waves are focused into a point through the omnidirectional lens effect imparted by the electromagnetic lens.

The reflection of the waves by the surface of the body is caused by the untuned impedance in the electromagnetic wave transmission system. Such variation in impedance is also generated at the reception side of the electromagnetic lens portion 12. In consequence, when viewed from the side of the driving antenna 11A, electromagnetic waves which have been reflected by both the electromagnetic lens portion 12 and the heated body surface can be detected. In such a case, the impedance of the electromagnetic lens portion 12 and the heated portion can be immediately tuned by adequately adjusting the stub tuner mechanism 13. This prevents the generation of standing waves caused by the reflected electromagnetic waves, thereby preventing the applicator from overheating and efficiently trasmitting electromagnetic energy into the heated portion of the body.

More specifically, the electromagnetic waves which have been propagated from the electromagnetic wave supply portion 11 through the casing 10 acting as a waveguide and which have been radiated toward the outside from the electromagnetic wave-radiating end portion 14 are reflected first by the electromagnetic lens portion 12 and then by the surface of the human body due to the untuned impedance, generating reflected waves r. In such a case, reflected wave r' is formed with respect to the electromagnetic wave supply portion 11 by employing the adjustable three stub tuning means. The r' is then set at −r (so that r' and −r have the same amplitude and opposite phase) by adjusting the three stub tuner mechanism 13. As a result, reflection r is cancelled by reflection r', thereby generating a reflectionless state when viewed from the electromagnetic wave supply portion 11 and ensuring that the load impedance is completely tuned. This eliminates most of the reflected waves, and the energy loss caused by the reflected waves can be reduced to a great extent.

Impedance tuning with the stub tuner mechanism 13 is actually conducted by an operaator by checking the reflection ratio which is displayed on the reflected wave display means (not shown) of a directional coupler connected to the coaxial connector 11B.

Apart from the impedance tuning effected by the stub tuner mechanism 13, a slight amount of energy loss is generated in the casing 10 due to the impedance of the electromagnetic wave transmission system. As a result, the casing 10 and the oil 10C are kept heated when the applicator is continuously used, thereby generating thermal expansion of the oil 10C. The expanded oil could damage the oil sealing screen 10D if left untreated. To cope with this problem, the oil release mechanism 16 acts to lead the thermally expanded portion of the oil 10C outside. The oil release mechanism 16 is also usable when replacing the oil 10C with new oil.

The electromagnetic lens portion 12 is so constructed that it can easily be replaced. Electromagnetic lens portions having different degrees of focusing are therefore selectively used to suit particular affected parts located at any depth within the human body, thereby enabling efficient hyperthermia.

In consequence, the applicator of the present invention makes a quick preparation operation possible when it is used for the treatment of various affected parts located at different depth, thereby ensuring a sufficient heating time. It is not necessary to prepare more than one of these applicators, and this makes the total cost of the apparatus used for hyperthermia relatively inexpensive.

Second Embodiment

A second embodiment of the present invention will now described with reference to FIGS. 13 to 15.

The applicator of this embodiment is different from that employed in the first embodiment in that improvement is made in the stub-tuning means 13 (see FIG. 2) and that the oil 10C is hermetically sealed.

Figure 13:
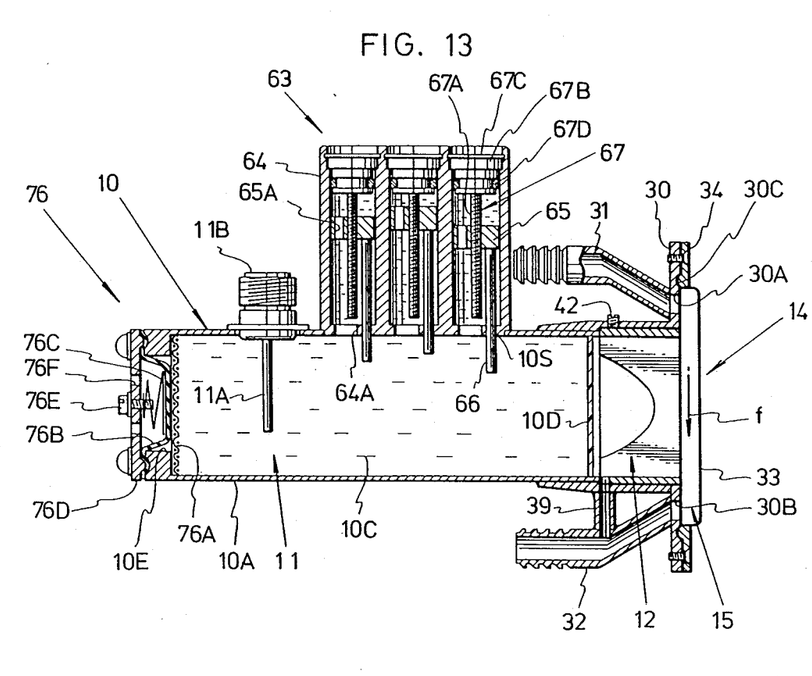
FIG. 13 is a sectional view of the applicator including the coolant guides, showing a second embodiment of the present invention.
Figure 14:
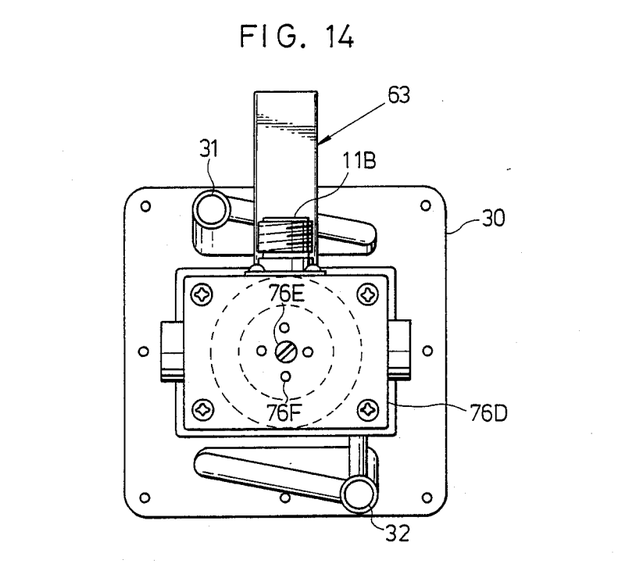
FIG. 14 is a side elevational view of the applicator shown in FIG. 13, as viewed from the left side of FIG. 13.
Figure 15:
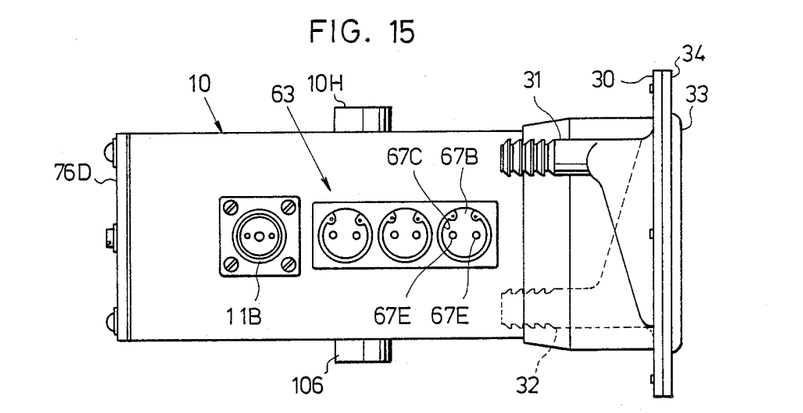
FIG. 15 is a plan view of the applicator shown in FIG. 13.

More specifically, reference numeral 10 in FIGS. 13 to 15 denotes a casing which functions as a wavequide as it does in the first embodiment. The casing 10 is provided with the electromagnetic wave supply portion 11 at one end thereof, the electromagnetic lens portion 12 at the other end, and a stub tuner mechanism 63 for stub-tuning electromagnetic waves at an intermediate portion thereof.

The stub tuner mechanism 63 is composed of three stub bars 66, each of which is capable of separately protruding into the casing 10 to an adequate extent.

To be more specific, the three stub tuners in the stub tuner mechanism 63 each include a cylinder portion 64 with one open end, a piston member 65 which moves back and forth in the cylinder portion 64, a stub bar 66 secured to a part of the piston member 65 and protruding in the casing through a predetermined through-hole 10S formed on the casing 10, a screw mechanism 67 rotatably mounted in the opening of the cylinder portion 64 for reciprocable moving piston member 65. The screw mechanism 67 is constructed with a driving screw portion 67A, a driving member 67B which fixes the driving screw portion 67A and is mounted in the cylinder portion 64 in such a manner that it is allowed only to rotate, a snap ring 67C which locks the driving member 67B in place, and a sealing member 67D mounted on the driving member 67B. As shown in FIG. 15, when the driving member 67B is rotated through two driving small holes 67E and 67E formed on the driving member 67B, the driving screw portion 67A which is integrally formed with the driving member 67B is rotated without its position changing to move the piston member 65 back and forth in the cylinder portion 64 by the counterforce of the rotation thereof. Thus, the amount that stub bar 66, which is integrally formed with the piston member 65, protrudes into the casing 10 is adjusted. Reference numerals 64A and 65A respectively denote oil circulating holes.

A fluid accommodating means 76 is provided at the left end portion of the casing 10 as viewed in FIG. 13. The fluid accommodating means 76 includes a fluid accommodating portion 10E occupying a certain space provided at the left end portion of the casing 10 as viewed in FIG. 13, a wire mesh 76A which has a small mesh size and separates the fluid accommodaating portion 10E and the supply portion waveguide 10A, a cup-shaped, resilient member 76B which has a recessed cross-section and is disposed in the fluid accommodating portion 10E by causing its central raised portion to be inserted in the fluid accommodating portion 10E from the outside, a coil spring 76C which constantly presses the cup-shaped soft member 76B at its central portion moderately toward the electromagnetic wave supply portion 11 from the outside, and a lid member 76D which locks the coil spring 76C and hermetically secures the cup-shaped soft member 76B in the casing 10. Reference numerals 76E and 76F designate a screw for locking the coil spring 76C and air holes formed on the lid member 76D, respectively.

The wire mesh 76A forms part of the side wall of the electromagnetic wave supply portion 11. Therefore, it may be replaced with, for example, a plurality of small holes provided directly in the inner wall of the electromagnetic wave supply portion 11, if they can be made to function in the same manner. A plate-like metal member having a large number of small holes may also be employed in place of the wire mesh 76A.

When the volume of the oil 10C is thermally expanded, as well as in the case of impedance tuning by means of the stub tuner mechanism 63, the fluid accommodating means 76 immediately acts to accommodate the increased portion of the oil 10C. In practical terms, the pressure of oil compresses the central portion of the cup-shaped soft member 76B so that the increased portion of oil is accommodated in the expanded portion of the fluid accommodating portion 10E.

The applicator of this embodiment is constructed in the same manner as that in the fact embodiment except for the above-described arrangements, as shown in FIGS. 13 to 15.

Thus, the applicator of this embodiment achieves the same effect as that provided by the applicator of the first embodiment. In addition to this, the applicator of the second embodiment makes it possible for a small amount of oil 10C to be pushed out into the casing 10 when the stub tuning means 63 is adjusted. This enables the use of a small-sized fluid accommodating means 76. It also allows the oil to be completely sealed, making an easily handled applicator possible.

The volume of the oil 10C increases as the temperature is raised, and the pressure of the oil C in the sealed container changes during the operation of the stub tuner mechanism 13 or 63. In the first and second embodiments, these occurrences are dealt with by providing the oil release mechanism 16 and the fluid accommodating means 76, respectively. However, when no adjustment of the stub tuner mechanism 13 or 63 is required, i.e., when the casing 10 is kept cooled from outside at a constant temperature and the applicator is used to treat the same affected part, it is not necessary to include the oil release mechanism 16 or the fluid accommodating means 76, provided the impedance is tuned beforehand.

What is claimed is:

1. An applicator for use in hyperthermia comprising:
   (a) a casing having an electromagnetic wave supply portion mounted on one axial end, and an electromagnetic lens portion and an electromagnetic wave radiating end portion having a free end at the other axial end;
   (b) a cooling mechanism on the free end of said electromagnetic wave radiating end portion for cooling the surface of a human body contacted by said radiating end portion; and
   (c) a stub tuner mechanism mounted on said casing between said electromagnetic wave supply portion and said electromagnetic lens portion, said stub tuner mechanism including a cylinder secured to said casing and having an open free end; a piston member reciprocably mounted in said cylinder; and a screw member operatively associated with said piston member for reciprocating the piston member in response to rotation of said screw member; said piston member having connected thereto a stub bar which projects into the casing through a hole therethrough for effecting an impedance tuning function.

2. An applicator according to claim 1 wherein said screw member comprises:
   (a) a driving screw member mounted in said cylinder for rotation only;
   (b) a driving screw portion rigidly connected to said driving screw member; and
   (c) said driving screw portion being threadably coupled to said piston member for effecting its reciprocation in said cylinder.

3. An applicator according to claim 2 including a liquid filling said electromagnetic wave supply portion and having a small damping factor with respect to electromagnetic waves, and a sealing member interposed between said cylinder and said driving screw member so as to make a liquid tight seal.

4. An applicator according to claim 1 wherein said electromagnetic wave supply portion is filled with a liquid having a small damping factor with respect to electromagnetic waves.

5. An applicator according to claim 4 including an expandable liquid accommodating means connected to the casing for effecting expansion of said liquid due to temperature changes.

6. An applicator according to claim 5 wherein said liquid accommodating means includes a space formed on a wall portion of said casing, means separating said space and said casing for allowing the communication of said liquid therethrough, a soft, resilient member adapted to close said separating means, said soft member being resiliently deformable for changing its shape, and means for biasing said soft member to said separating means in order to normally close the communication of the liquid.

* * * * *

UNITED STATES PATENT AND TRADEMARK OFFICE
CERTIFICATE OF CORRECTION

PATENT NO. : 4,841,990

DATED : June 27, 1989

INVENTOR(S) : M. KIKUCHI et al.

It is certified that error appears in the above-identified patent and that said Letters Patent is hereby corrected as shown below:

at column 1, line 14, change "Researches" to ---research---;
at column 1, line 32, change "waaves" to ---waves---;
at column 3, line 17, change "a a" to ---a---;
at column 4, line 51, change "As" to ---An--- before "affected";
at column 5, line 16, change "moves" to ---move---;
at column 6, line 2, change "operaator" to ---operator---;
at column 6, line 27, change "depth" to ---depths---;
at column 6, line 40, change "wavequide" to ---waveguide---;
at column 6, line 58, change "reciprocable" to ---reciprocably---;
at column 7, line 17, insert ---soft,--- before "resilient"; and
at column 7, line 48, change "fact" to ---first---.

Signed and Sealed this

Fourth Day of August, 1992

Attest:

DOUGLAS B. COMER

*Attesting Officer*  *Acting Commissioner of Patents and Trademarks*